United States Patent [19]

Pakhomov et al.

[11] 4,424,203

[45] Jan. 3, 1984

[54] GEL FOR DENTAL CARIES PREVENTION

[76] Inventors: Gennady N. Pakhomov, Leninsky prospekt 123/1, kv. 529, Moscow; Anita Y. Luste, ulitsa Lachplesha 27, kv. 22, Riga; Anatoly G. Kolesnik, ulitsa Shosseinaya 58, korpus 2, kv. 59, Moscow; Vasily N. Demishev, Leninsky prospekt 67, kv. 230, Moscow; Eva L. Pashinina, ulitsa Novolesnaya 7, korpus 2, kv. 20, Moscow; Maria V. Mordvinova, ulitsa Novye Cheremushki 24-a, korpus 1, kv. 9, Moscow; Lilia V. Morozova, ulitsa Krasnogo Mayaka 8, korpus 2, kv. 264, Moscow; Lidia M. Boginskaya, Odintsovo-2, Mozhaiskoe shosse 49, kv. 232, Moskovskaya oblast; Irina B. Voskresenskaya, prospekt Pravdy 5, kv. 128; Sara Z. Osadchuk, prospekt Traktorostroitelei 162, kv. 141, both of Kharkov; Galina I. Kadnikova, ulitsa Ya. Rudzutaka 60, kv. 10, Riga, all of U.S.S.R.

[21] Appl. No.: 472,213

[22] Filed: Mar. 4, 1983

[51] Int. Cl.$^3$ ................. A61K 7/18; A61K 33/16; A61K 35/32

[52] U.S. Cl. ........................ 424/52; 424/49; 424/57; 424/95; 424/151

[58] Field of Search .................. 424/49–58, 424/95, 151

[56] References Cited

U.S. PATENT DOCUMENTS

| 1,664,182 | 3/1928 | Parisi | 424/95 |
|---|---|---|---|
| 2,154,168 | 4/1939 | Klein et al. | 424/57 |
| 2,968,593 | 1/1961 | Rapkin | 424/95 |
| 3,743,721 | 7/1973 | Mattox | 424/95 |
| 4,172,128 | 10/1979 | Thiele et al. | 424/95 |
| 4,327,079 | 4/1982 | Aoki | 424/57 |
| 4,342,741 | 8/1982 | Aoki | 424/57 |
| 4,357,317 | 11/1982 | Weyn et al. | 424/52 |

FOREIGN PATENT DOCUMENTS 674909  7/1952  United Kingdom ............ 424/95

*Primary Examiner*—Shep K. Rose
*Attorney, Agent, or Firm*—Burgess, Ryan & Wayne

[57] ABSTRACT

A gel for dental caries prevention is disclosed, comprising a gelling agent, a humectant, a surface active material, a flavoring material, 1.7–11% by weight of an anticaries agent which is a mixture of sodium monofluorophosphate with a substance obtained from treating the bone tissue with a diluted mineral acid to completely remove the mineral components and water-soluble proteins contained in bone tissue, isolation of the thus obtained solution, diluting it with water and stabilizing additives of citric acid or salts thereof, with subsequent neutralization of the solution and drying, and including the following parts and proportions by weight %:

| | |
|---|---|
| calcium | 2–6 |
| sodium | 19–23 |
| potassium | 0.04–0.18 |
| anion of mineral acid | 6–10.6 |
| anion of orthophosphoric acid | 1.5–5.0 |
| water-soluble proteins | 1.0–5.0 |
| magnesium | 0.05–0.2 |
| complex of microelements including fluorine, manganese, tin, zinc, iron | 0.01–0.02 |
| complex citrate compounds calculated for citric acid anion | the rest. |

4 Claims, No Drawings

GEL FOR DENTAL CARIES PREVENTION

FIELD OF THE INVENTION

This invention relates to dentistry and, more particularly, to a gel for dental caries prevention employed in daily oral hygiene as well as exerting an antiinflammatory effect in periodontal diseases and an analgesic effect on dentin hyperesthesia. Moreover, this gel is useful in large-scale campaigns to prevent tooth decay both in social groups of children (such as schools, nursery homes, etc.) and on an outpatient basis which involve mainly pregnant women and children with an active form of caries.

BACKGROUND OF THE INVENTION

Dental media possessing curative and prophylactic properties are known in a variety of forms such as toothpastes, elixirs, gels, dental powders, lacquers, tablets. In a number of cases due to a high degree of abrasiveness toothpastes may be replaced by gels. For example, a known gel contains a gelling agent, a humectant, a surface active agent and a flavouring substance. Furthermore, the gel vehicle may be dyed and contain polyvalent metal salts and hydroxides such as aluminum sulphate, calcium hydroxide, stannous bifluoride, ferrum sulphate and cadmium sulphate (UK Pat. No. 1,309,026 issued Mar. 7, 1973). Furthermore, in the past a polishing agent has been added to the gel vehicle. The composition of such a polishing agent included calcium carbonate, fluoride ions and monofluorophosphate ions generally in amounts of 40–80% and 20–60%, respectively, of the total fluorine content of the composition. This content is in the range of 40–55% and 45–60%, respectively, of the total fluorine content. Fluorine content of the gel varies between 0.025–0.2%, preferably 0.05–0.12% by weight of the composition (French Patent No. 2,251,309, issued July 18, 1975). Another known fluoride gel capable of preventing dental caries contains a solution of a water-soluble source of fluoride ions gelled with gum xanthene. The water-soluble source of fluoride ions may be sodium fluoride, potassium or tin fluoride, titanium tetrafluoride, sodium monofluorophosphate or an amino fluoride. Generally, the water solution is a solution of sodium fluoride, hydrofluoric acid and orthophosphoric acid (application Ser. No. 1,450,881, issued 1976, IX, UK).

Another gel of curative and prophylactic value used in the dental practice is known by its proprietary name "Fluocaril" (France) and is capable of combating caries formation comprising the following components in weight %:

| sodium benzoate | 4.0 |
| eugenol | 0.025 |
| paraoxymethylbenzoate | 0.1 |
| sodium monofluorophosphate | 0.570 |
| sodium fluoride | 0.055 |
| gelling agent | up to 100.00 |

(total concentration of fluorine ions—0.1%). (Advertisment bulletin "Fluocaril" Lab. Goupil. S. A.).

A disadvantage commonly associated with the above dental gels is their low anticaries efficacy.

SUMMARY OF THE INVENTION

It is the main object of this invention to provide a dental gel of high anticaries activity which would promote calcification of the least resistant areas of wedge-shaped defects, erosions, acidic necrosis and local demineralization.

It is a further object of this invention to provide a dental gel having an anti-inflammatory and analgesic action and agreeable smell and taste.

In seeking to achieve these objects we have provided a dental gel with a beneficial anticaries effect comprising a gelling agent, a humectant, a surface active material, a flavouring material, a substance active against caries development containing sodium monofluorophosphate, according to the invention, the composition includes 1.7–11% by weight of the anticaries substance which is a mixture of sodium monofluorophosphate with a substance obtained from treating the bone tissue with a diluted mineral acid to completely remove the mineral components and water-soluble proteins contained in the bone tissue, isolation of the thus obtained solution, diluting it with water and stabilizing additives of citric acid or salts thereof, with subsequent neutralization of the solution and drying, and including the following parts and proportions by weight %:

| calcium | 2–6 |
| sodium | 19–23 |
| potassium | 0.04–0.18 |
| anion of mineral acid (chloride) | 6–10.6 |
| anion of orthophosphoric acid | 1.5–5.0 |
| water-soluble proteins | 1.0–5.0 |
| magnesium | 0.05–0.2 |
| complex of microelements including fluorine, manganese, tin, zinc, iron | 0.01–0.02 |
| complex citrate compounds calculated for citric acid anion | the rest. |

It is desirable that the dental gel include sodium carboxymethylcellulose or a co-polymer of tetraallylpentaerythrate acrylic acid as a gelling agent. If the selected gelling agent is sodium carboxymethylcellulose, the dental gel will contain additives in the form of a preservative incorporated in the following proportion of the constituent parts in weight %:

| sodium carboxymethylcellulose | 2.0–4.5 |
| glycerin | 10.0–20.0 |
| surface active agent | 0.9–1.1 |
| sodium monofluorophosphate | 0.7–5.0 |
| anticaries agent | 1.0–6.0 |
| flavour | 0.9–1.0 |
| preservative | 0.05–0.1 |
| water | the rest. |

If the selected gelling agent is a co-polymer of tetraallylpentaerythrate acrylic acid, the dental gel has the following composition in weight %:

| co-polymer of tetraallylpentaerythrate acrylic acid | 2.0–4.5 |
| glycerin | 10.0–20.0 |
| surface active agent | 0.9–1.1 |
| sodium monofluorophosphate | 0.7–5.0 |
| anticaries agent | 1.0–6.0 |
| flavour | 0.9–1.0 |
| water | the rest |
| at pH | 6.5–7.5 |

DETAILED DESCRIPTION OF THE INVENTION

The gel of this invention is a transparent colorless mass with an agreeable smell and taste retaining its properties over one year in storage. The curative and prophylactic value of the gel is derived from experimentally formulating its constituent parts in a certain proportion. Addition of sodium monofluorophosphate in amount over 5.0 weight % results in a fluoride ion concentration in excess of 0.6% which may lead to dental fluorosis following regular use of the gel. Addition of sodium monofluorophosphate in amounts below 0.7% by weight impairs the curative and prophylactic properties of the gel. With the anticaries agent content over 6.0% the gel vehicle acquires excessive density and irregularly distributed viscosity, moreover, it adversely affects its foam forming, curative and prophylactic properties. With the anticaries agent content falling below 1.0% by weight the gel vehicle becomes excessively liquid with diminished curative and prophylactic properties. When the selected gelling agent is the co-polymer of tetraallylpentaerythrate acrylic acid, the gel vehicle is added with an alkali to adjust the pH to 6.5-7.5. The preservative content of less than 0.05% by weight results in deterioration of the gel quality, whereas an increase in the preservative concentration above 0.1% is undesirable. The gel of this invention effectively interferes with caries formation. The gel produces mineralization of the enamel in wedge-shaped defects and various forms of enamel demineralization. The use of the composition to combat foci demineralization proved successful in 72.5% of cases. The novel gel was shown to exert 1.5-2 times the anticaries activity of the known gel "Fluocaril". Animal experimentation and clinical trials on humans involved the use of the gel according to this invention and the anticaries agent incorporated therein.

A test with a 3% solution of the anticaries agent was conducted against a control series. 80 Wistar rats one-month of age were entered on study (40 individuals received the trial solution, the remaining 40 constituting controls). All rats were put on Stephan 580 cariogenic diet with daily three minute topical applications of the trial substances to the teeth continued for four weeks. The teeth were removed upon completion of the study and used to determine the caries index by the conventional method. The results of this experiment are listed in Table 1.

The efficacy of preventing tooth decay following use of the anticaries agent in the form of a 3% solution for topical applications continued at least 1.5 years in a two times daily regimen in children 7-10 years old was evaluated by the relative drop in the DMF-T index increment from 33.1 to 53.7%, and that of DMF-S- from 40.2 to 58.0%, the CRT-test findings showing a substantial increase in the enamel's acid resistance.

Efficacy of the 3% anticaries agent in the treatment of incipient caries is high, while the therapeutic success defined as complete disappearance or diminution of demineralized spots was noted in 72.4-84%, the condition was effectively controlled in 14-31.9%, response failed to emerge in 2-8% of cases.

Efficacy of the 3% solution of the anticaries agent experienced in the treatment of dental hyperesthesia was significant with full relief of increased sensitivity in the tooth neck in 23.2-36.4% of cases.

A clinical trial of the anticaries agent was conducted in order to look into its prophylactic action in children and pregnant women subjects as well as to study its efficacy in conservative treatment of local demineralization affecting the dental enamel. The anticaries agent was employed in the form of 1.5-3% solutions for topical application.

176 children in the age of between 7 and 8 years were selected for study by the results of epidemiological examination. The children were divided into two groups:

Group I included the children receiving applications of the anticaries solution—81 subject;

Group II constituted controls—95 subjects.

Applications of the solution were performed subsequent to cleaning the teeth with a toothpaste. The teeth were then cleaned of saliva with swabs of lignin and dried by a stream of air. Using spoons made from a flexible plastic material and containing soaked loosely packed cotton tampons, the solution was applied to the entire surface of the teeth. Each application continued for 10 minutes per one jaw. On completion of the procedure the children were advised to abstain from food for two hours. The identical technique was used in all subsequent applications repeated once every two weeks.

The initial examination of the oral cavity indicated a relatively uniform level of caries attack ranging from $1.12\pm0.13$ to $1.30\pm0.13$ as given by DMF-T index.

The results of using the anticaries solution are reflected in Table 2.

TABLE 1

Data comparing anticarious efficacy of the anticaries agent solution according to the invention with the control

| Nos | Substance under study (group) | Caries index in fissure areas | Anticaries efficacy, % | Caries index in contact areas | Anticaries efficacy, % | Total caries index in all areas | Anticaries efficacy, % |
|---|---|---|---|---|---|---|---|
| 1 | 2 | 3 | 4 | 5 | 6 | 7 | 8 |
| 2 | Control group | 26.75 | — | 2.76 | — | 29.51 | — |
| 3 | Anticaries agent solution of the invention | 20.42 | 23.7 | 1.00 | 63.7 | 21.42 | 27.4 |

TABLE 2

| Nos | Group No | Prophylactic measures | Number of examined subjects | Indices following one year of observation | | | | Number of examined subjects | Indices following three years of observation | | | |
|---|---|---|---|---|---|---|---|---|---|---|---|---|
| | | | | Increment of | | Increment reduction, % | | | Increment | | Increment reduction, % | |
| | | | | DMF-T | DMF-S | DMF-T | DMF-S | | DMF-T | DMF-S | DMF-T | DMF-S |
| 1 | 2 | 3 | 4 | 5 | 6 | 7 | 8 | 9 | 10 | 11 | 12 | 13 |
| 2 | I | Application of remineralizing solution of the trial agent to teeth | 81 | 0.78 ± 0.16 | 1.12 ± 0.28 | 19.6 | 22.7 | 81 | 1.61 ± 0.18 | 2.59 ± 0.34 | 44.7 | 49.5 |
| 3 | II | Control | 95 | 0.97 ± | 1.45 ± | — | — | 78 | 2.91 ± 0.16 | 5.13 ± 0.25 | — | — |

It will be apparent from the foregoing table that the reduction increment in the first group of children was 44.7 and 49.5%, respectively, as estimated by DMF-T and DMF-S indices.

Analysis of the trial substance's ability to stop caries development with respect to specific groups of teeth assessed its effect on the molars whose eruption preceded the start of investigation as well as on the incisors erupting at the time of observation.

A solution of the trial substance was used in the treatment of dental demineralization in 81 children of school age ranging between 7 and 14 years.

The children were distributed into two sub-groups depending on the form of demineralization:

3a group was made up of children with slow developing forms of demineralization (total of 42 school children);

3b group was composed of children with rapidly progressive forms of demineralization (total of 39 school children).

All in all, demineralization was detected in 229 teeth of children from 3a group and 248 teeth of children from 3b group (table 3). Controls were made up of the children from the previous observation series designated in the table as groups 1a and 1b.

To attain positive response to treating teeth with the studied substance solution, the mean number of applications required was in 3a group—10–15 applications, and in 3b group—20–25.

TABLE 3

Number of teeth in children of group 3 and group 1 (controls) with demineralization foci depending on their size

| Nos | Spot size | 1a control group | 1b control group | 3a group | 3b group |
|---|---|---|---|---|---|
| 1 | 2 | 3 | 4 | 5 | 6 |
| 2 | <2 mm$^2$ | 73 | 48 | 81 | 24 |
| 3 | 2–3 mm$^2$ | 125 | 102 | 117 | 120 |
| 4 | >3 mm$^2$ | 81 | 155 | 31 | 104 |
| 5 | Total spots | 279 | 305 | 229 | 248 |

Remineralization therapy was more efficient against slow developing forms of demineralization. In particular, small size spots (2 mm$^2$ and 2–3 mm$^2$) disappeared or diminished more rapidly than those of bigger size. Conservative treatment of rapidly progressive demineralization affecting the teeth in children from group 3b was less dramatic; however, a direct relation between the degree or attained response and the size of spots involved held good for that group also (Table 4).

The positive therapeutic response defined as disappearance of spots in group 3a was noted in 193 teeth out of the total 229 (84%±2.4) compared with the controls where similar results were observed in only 100 teeth out of 270 (36%±2.9).

Stabilization of the process in group 3a was documented in 31 teeth (14%±6.23) and in 87 teeth (31%±2.8) of the control group.

Enlargement of the spots and cavitation in group 3a occurred only in 5 teeth of 229 (2%±0.9) and in 92 of 279 (33%±2.8) of the controls.

The difference between the indices of group 3a and control group 1a are statistically significant (Table 4).

In group 3b, treatment of rapidly progressive demineralization resulted in a positive response in 155 of 248 teeth (63%±3.0), whereas in the control group, spontaneous recession was noted in 33 of 305 teeth, therefore, making up only 11%±1.8. In 60 teeth of children from group 3b (24%±2.7), the process was effectively contained. In the area of focal demineralization in 33 teeth (13%±2.1) of children from group 3b, there was resultant cavitation.

Differences between the indices of group 3b and control group 1b are statistically significant (Table 4).

Therefore, the mean positive response to the treatment of slow and rapidly progressive forms of demineralization affecting the enamel is 73.5%.

A trial series with a solution of the anticaries agent was conducted on pregnant women. Epidemiological investigation of pregnant women showed that with increased gestation time, the extent and intensity of focal demineralization affecting the dental enamel also increase. To prevent such spread of desintegration in 69 (group I) pregnant women, a solution of the agent according to this invention was utilized in the form of topical applications. 64 other pregnant women constituted the controls (group II).

The study involving both groups of women (1–3 months of gestation) revealed comparable levels of dental attack by focal demineralization—29–30% with a mean involvement of 1.8±0.3 teeth.

By the end of gestation in women from the control group, focal demineralization of the dental enamel affected 64% of cases with a mean value of 5.23±0.7 teeth.

The use of the anticaries agent according to this invention in women subjects of group I permitted not only prevention of further focal lesions of the enamel but stabilization of the caries process in the already existing foci (which did not increase in size or lead to cavity formation).

Another series of tests centered on the gel vehicle of this invention. To this end, two gel compositions formulated according to this invention contained the following active components—first: 1% anticaries agent and 0.7% sodium monofluorophosphate; second: 6% anticaries agent and 5% sodium monofluorophosphate. The test was contrasted with a placebo gel.

Abrasiveness of the dental gel compositions and placebo gel (with abrasive) was evaluated using 15 human teeth removed for medical reasons. The abrasive value of the placebo gel was designated as the unity (results summarized in Table 5).

The aforementioned composition of gels and placebo gel were studied on 100 Wistar rats one month old (25 rats per every composition and 25 making up the controls), maintained on a special diet productive of drastic hypocalcification of the enamel occurring with durations of experiment of up to six weeks. The gel of this invention and its placebo counterpart were both used daily for cleaning the animals' teeth for one minute. On completion of the experiment, jaw blocks were removed and those pertaining to the mandible used to determine the hypocalcification index according to Francis' method (Francis H. D. Arch. oral. Biol., 1966, 11, 141–148). The teeth of the upper jaw were used to determine the fluorine content in the superficial enamel layer. Subsequently, a percent reduction in the hypocalcification index was computed with respect to the control group while an increase in the fluorine content of the superficial enamel layer was calculated compared to rat teeth from the control group (data are given in Table 5).

A study of the influence of the tested agents on $Ca^{45}$ permeability into the dental enamel was conducted on 32 teeth (canines) of 8 dogs 3–4 years old following a single one hour long application with subsequent mathematical analysis. That was followed by computation of a percent decrease in permeability (data are listed in Table 5).

The test results summarized in the table clearly show that both alternative compositions of the gel according to this invention exert a pronounced action on the state of calcified dental tissues. First, the abrasiveness of dental gels is very low which avoids undue mechanical wear of the dental enamel when brushing teeth of special concern in cases of enamel highly susceptible to abrasion and wedge-shaped defects. The dental gel of this invention drastically reduces the index of enamel hypocalcification and permeability, and at the same time sharply increases the fluorine content of the superficial enamel layer along with its resistance to the action of adverse factors, hence its use is advisable not only in instances of excessive susceptibility to abrasion on the part of the enamel and wedge-shaped defects, but also in various forms of enamel decalcification. The effect thus produced is the stronger, the greater the concentration of the anticaries agent and sodium monofluorophosphate incorporated in the gel.

TABLE 4

Results of treating teeth with recalcifying solution of the trial anticaries agent in children

| | | Characterization of demineralization foci Distribution of spots in children of group 3a | | | | | Characterization of mineralization foci Distribution of spots in children of group 3b | | | | |
|---|---|---|---|---|---|---|---|---|---|---|---|
| | | by size | | | by number | compared to | by size | | | by number | compared to |
| Nos | Outcome of treating dental enamel demineralization | <2 mm² | 2–3 mm² | >3 mm² | Abs. | M ± m, % | controls (p < 0.001) | <2 mm² | 2–3 mm² | >3 mm² | Abs. | M ± m, % | controls (p < 0.001) |
| 1 | 2 | 3 | 4 | 5 | 6 | 7 | 8 | 9 | 10 | 11 | 12 | 13 | 14 |
| 2 | Complete disappearance of spots | 64 | 98 | 31 | 193 | 84 ± 2.4 | 10.8 | 19 | 73 | 63 | 255 | 63 ± 3.0 | 12.8 |
| 3 | Stabilization of caries process | 13 | 18 | — | 31 | 14 ± 2.3 | 4.5 | 1 | 31 | 23 | 60 | 24 ± 2.7 | 3.4 |
| 4 | Formation of defects | 4 | 1 | — | 5 | 2 ± 0.9 | 8.9 | 4 | 16 | 13 | 33 | 13 ± 2.1 | 14.7 |
| 5 | Total | | | | 229 | 100 | | | | | 248 | 100 | |

TABLE 5

Comparative data on properties of two alternative dental gel compositions, placebo gel and "Fluocaril" gel (France)

| | | Concentration in weight % | | | | Indices | | | | |
|---|---|---|---|---|---|---|---|---|---|---|
| Nos | Names of agent | anticaries agent | Na₂PO₃F | NaF | Abrasiveness in rel. units | Percent drop in hypocalcification index | Increment of fluorine content of superficial enamel layer in weight % | Percent drop in $Ca^{45}$ permeability of the enamel | caries index | anticaries efficacy, % |
| 1 | 2 | 3 | 4 | 5 | 6 | 7 | 8 | 9 | 10 | 11 |
| 2 | placebo dental gel (with abrasive) | — | — | — | 1.00 (100%) | 6.2 | 0.0012 | 3.3 | 37.54 ± 0.85 | — |
| 3 | dental gel of this invention | 1.00 | 0.7 | — | 0.01 (1%) | 31.6 | 0.0154 | 20.6 | 22.64 ± 1.05 | 39.70 |
| | | 6.00 | 5.0 | — | 0.02 (2%) | 41.2 | 0.0283 | 37.2 | 16.12 ± 1.01 | 57.00 |
| 4 | Gel "Fluo- | — | 11.4 | 1.1 | | | 0.0357 | | 27.78 ± | 26.00 |

TABLE 5-continued

Comparative data on properties of two alternative dental gel compositions, placebo gel and "Fluocaril" gel (France)

| Nos | Names of agent | Concentration in weight % anticaries agent | Na₂PO₃F | NaF | Abrasiveness in rel. units | Percent drop in hypocalcification index | Increment of fluorine content of superficial enamel layer in weight % | Percent drop in Ca⁴⁵ permeability of the enamel | caries index | anticaries efficacy, % |
|---|---|---|---|---|---|---|---|---|---|---|
| | caril" | | | | | | | | 1.12 | |

Following daily cleaning of teeth with the gel of the novel composition during a period of six weeks at the maximal concentrations of sodium monofluorophosphate and anticaries agent therein, the hypocalcification index of the dental enamel drops by 17.59±0.69 which corresponds to 41.2% and less of the control (cleaning with the placebo gel) by 35% (17.59±0.69 and 28.01±0.53, respectively). Following daily cleaning of teeth with the gel composition according to this invention during six weeks at the minimal concentrations of sodium monofluorophosphate and anticaries agent therein, the hypocalcification index of the enamel drops by 20.43±0.61 which makes up 31.6% and less of the placebo control by 25.4% (20.43±0.61 and 28.01±0.53, respectively).

The increment in the fluorine content of the superficial enamel layer following the use of the gel with peak concentrations of sodium monofluorophosphate and anticaries agent is 0.0283% by weight, and following the use of the gel with the minimal concentrations of sodium monofluorophosphate and anticaries agent—0.0154% by weight, finally, with placebo gel—0.0012% by weight.

The enamel permeability in dogs following use of the gel with the maximal concentrations of sodium monofluorophosphate and anticaries agent drops by 37.2%, that for the gel with minimal concentrations of sodium monofluorophosphate and anticaries agent—by 20.6%, whereas the placebo gel—by 3.3%.

The gel with the maximal concentration of sodium monofluorophosphate and anticaries agent has an abrasiveness of less than or equal to 2%, gel with the minimal concentrations of sodium monofluorophosphate and anticaries agent exhibits the aforementioned characteristic of 1%, and the placebo gel with an abrasive—100%.

The gel of this invention is capable of calcifying the enamel in various forms of enamel decalcification. Use of the agent to combat foci of decalcification elicits a beneficial response in 73.5% of cases.

In addition to a comparative test with the placebo gel, similar comparison was made with respect to the gel "Fluocaril", manufactured in France. The gel of this invention was shown to have 1.5–2.2 times the anticaries efficacy of the gel "Fluocaril".

The gel of this invention is produced by mixing the gelling agent with the humectant to obtain a jellylike mass, then introducing the gel components. Introduction of each successive component is followed by stirring, milling and expelling the residual bubbles of air. If the selected gelling agent is a co-polymer of tetraallylpentaerythrate acrylic acid, the mixture is added with an alkali, for example, caustic soda or potassium hydroxide or threeethalomine to adjust the pH value to 6.5–7.5. The anticaries agent incorporated in the gel vehicle is prepared in the following manner. The bone tissue is immersed in a dilute mineral acid and kept there under agitation to completely dissolve the mineral components and water-soluble proteins incorporated in the bone tissue. The thus obtained solution is then isolated and diluted with water with stabilizing additives of citric acid or salts thereof. The solution is subsequently neutralized. To facilitate transportation and storage, the agent is manufactured in dry form. For that purpose, the solution is sprayed in a drier. The resultant powder appearing as a white amorphous odourless substance with a brackish taste readily soluble in water is only slightly soluble in a 95% alcohol and virtually insoluble in ether.

In order that this invention be more fully understood, the following dental gel for caries prevention is hereinbelow put forward by way of illustration.

EXAMPLE 1

A gel for dental caries prevention having the following composition in grams:

| | |
|---|---|
| sodium carboxymethylcellulose | 2.00 |
| glycerin | 19.95 |
| sodium laurylsulphate | 1.00 |
| sodium monofluorophosphate | 0.70 |
| anticaries agent including the following constituent parts in % by weight: | 1.00 |
| calcium | 6.00 |
| anion of orthophosphoric acid | 5.00 |
| sodium | 19.00 |
| magnesium | 0.05 |
| potassium | 0.04 |
| anion of mineral acid (chloride) | 6.00 |
| complex of microelements | 0.01 |
| water-soluble proteins | 1.00 |
| complex citrate compounds calculated for citric acid anion | 63.90 |
| paraform | 0.10 |
| flavour | 1.00 |
| water | up to 100.00 |

The gel of this invention is obtained by mixing glycerin with a humectant, the latter being sodium carboxymethylcellulose. The thus obtained mixture is agitated to produce a jellylike mass. The remaining gel components are added in such a manner that introduction of each successive ingredient is followed by stirring, milling and expelling the residual bubbles of air.

| | |
|---|---|
| Dynamic yield strength | 300 dyne/cm² |
| Coefficient of plasticity | 20.5. |

EXAMPLE 2

A gel for dental caries prevention having the following composition in grams:

| | |
|---|---|
| sodium carboxymethylcellulose | 4.50 |
| glycerin | 15.20 |
| sodium laurylsulphate | 1.00 |
| sodium monofluorophosphate | 5.00 |
| anticarie agent including the following constituent parts in % by weight: | 6.00 |
| calcium | 2.00 |
| anion of orthophosphoric acid | 1.90 |
| sodium | 23.00 |
| magnesium | 0.20 |
| potassium | 0.18 |
| anion of mineral acid (chloride) | 10.60 |
| complex of microelements | 0.02 |
| water-soluble proteins | 5.00 |
| complex citrate compounds calculated for citric acid anion | 57.10 |
| chlorogexidine | 0.05 |
| flavour | 0.80 |
| water | up to 100.00 |

The gel of this Example is obtained as described in Example 1.

| | |
|---|---|
| Dynamic yield strength | 400 dyne/cm$^2$ |
| Coefficient of plasticity | 23.5. |

EXAMPLE 3

A gel for dental caries prevention having the following composition in grams:

| | |
|---|---|
| sodium carboxymethylcellulose | 3.00 |
| glycerin | 17.25 |
| sodium laurylsulphate | 1.10 |
| sodium monofluorophosphate | 4.50 |
| anticaries agent including the following constituent parts in % by weight: | 3.00 |
| calcium | 4.00 |
| anion of orthophosphoric acid | 3.92 |
| sodium | 21.20 |
| magnesium | 0.14 |
| potassium | 0.12 |
| anion of mineral acid (chloride) | 8.20 |
| complex of microelements | 0.02 |
| water-soluble proteins | 3.00 |
| complex citrate compounds calculated for citric acid anion | 59.40 |
| chlorogexidine | 0.05 |
| flavour | 1.20 |
| water | up to 100.00 |

The gel of this Example is obtained as described in Example 1.

| | |
|---|---|
| Dynamic yield strength | 375 dyne/cm$^2$ |
| Coefficient of plasticity | 23.5. |

EXAMPLE 4

A gel for dental caries prevention having the following composition in grams:

| | |
|---|---|
| co-polymer of tetraallylpentaerythrate acrylic acid | 2.00 |
| glycerin | 19.95 |
| sodium laurylsulphate | 1.00 |
| sodium monofluorophosphate | 0.70 |
| anticaries agent including the following constituent parts in % by weight: | 1.00 |
| calcium | 3.50 |
| anion of orthophosphoric acid | 5.00 |
| sodium | 20.20 |
| magnesium | 0.18 |
| potassium | 0.15 |
| anion of mineral acid (chloride) | 7.95 |
| complex of microelements | 0.02 |
| water-soluble proteins | 1.10 |
| complex citrate compounds calculated for citric acid anion | 61.90 |
| flavour | 1.00 |
| water | up to 100.00 |

The gel of this Example is obtained as follows. Glycerin is added with the co-polymer of tetraallylpentaerythrate acrylic acid with agitation until a jellylike mass has been formed. The remaining components of the gel are then added, each successive ingredient introduction being followed by stirring and neutralization up to a pH value of 6.5–7.5. Neutralization can be effected with a solution of caustic soda or potassium hydroxide or threeethanolamine. The thus obtained jellylike mass is added with the anticaries agent and then stirred, milled and vacuum treated to expel the residual air bubbles.

| | |
|---|---|
| Dynamic yield strength | 310 dyne/cm$^2$ |
| Coefficient of plasticity | 21.5. |

EXAMPLE 5

A gel for dental caries prevention having the following composition in grams:

| | |
|---|---|
| co-polymer of tetraallylpentaerythrate acrylic acid | 4.50 |
| glycerin | 15.20 |
| sodium laurylsulphate | 1.00 |
| sodium monofluorophosphate | 5.00 |
| anticaries agent including the following constituent parts in % by weight: | 6.00 |
| calcium | 3.20 |
| anion of orthophosphoric acid | 4.90 |
| sodium | 22.00 |
| magnesium | 0.18 |
| potassium | 0.17 |
| anion of mineral acid (chloride) | 8.95 |
| complex of microelements | 0.02 |
| water-soluble proteins | 1.10 |
| complex citrate compounds calculated for citric acid anion | 59.48 |
| flavour | 1.00 |
| water | up to 100.00 |

The gel of this Example is obtained as described in Example 4.

| | |
|---|---|
| Dynamic yield strength | 390 dyne/cm$^2$ |
| Coefficient of plasticity | 24.5. |

EXAMPLE 6

A gel for dental caries prevention having the following composition in grams:

| | |
|---|---|
| co-polymer of tetraallylpentaerythrate acrylic acid | 3.00 |

-continued

| | |
|---|---|
| glycerin | 17.25 |
| sodium laurylsulphate | 1.10 |
| sodium monofluorophosphate | 4.50 |
| anticaries agent including the following constituent parts in % by weight: | 3.00 |
| calcium | 3.80 |
| anion of orthophosphoric acid | 5.00 |
| sodium | 22.80 |
| magnesium | 0.20 |
| potassium | 0.18 |
| anion of mineral acid (chloride) | 8.88 |
| complex of microelements | 0.02 |
| water-soluble proteins | 1.36 |
| complex citrate compounds calculated for citric acid anion | 57.76 |
| flavour | 1.20 |
| water | up to 100.00 |

The gel of this Example is obtained as described in Example 4.

| | |
|---|---|
| Dynamic yield strength | 370 dyne/cm$^2$ |
| Coefficient of plasticity | 23.0 |

We claim:

1. A gel for dental caries prevention comprising a gelling agent, a humectant, a surface active substance, a flavouring agent, 1.7–11% by weight of an anticaries agent which is a mixture of sodium monofluorophosphate with a substance obtained from treating the bone tissue with a dilute mineral acid to completely remove the mineral components and water-soluble proteins contained in the bone tissue, isolation of the thus obtained solution, diluting it with water and stabilizing additives of citric acid or salts thereof, with subsequent neutralization of the solution and drying, and including the following parts and proportions by weight %:

| | |
|---|---|
| calcium | 2–6 |
| sodium | 19–23 |
| potassium | 0.04–0.18 |
| anion of mineral acid (chloride) | 6–10.6 |
| anion of orthophosphoric acid | 1.5–5.0 |
| water-soluble proteins | 1.0–5.0 |
| magnesium | 0.05–0.2 |
| complex of microelements including fluorine, manganese, tin, zinc, iron | 0.01–0.02 |
| complex citrate compounds calculated for citric acid anion | the rest. |

2. A gel for dental caries prevention as claimed in claim 1, wherein the gelling agent comprises a substance selected from a group of substances including sodium carboxymethylcellulose, and a co-polymer of tetraallylpentaerythrate acrylic acid.

3. A gel for dental caries prevention as claimed in claim 2, comprising sodium carbonylmethylcellulose as the gelling agent and, additionally, a preservative in the following proportion of the starting components by weight %:

| | |
|---|---|
| sodium carboxymethylcellulose | 2.0–4.5 |
| glycerin | 10.0–20.0 |
| surface active agent | 0.9–1.1 |
| sodium monofluorophosphate | 0.7–5.0 |
| anticaries agent | 1.0–6.0 |
| flavour | 0.9–1.0 |
| preservative | 0.05–0.1 |
| water | the rest. |

4. A gel for dental caries prevention as claimed in claim 2, comprising a co-polymer of tetraallylpentaerythrate acrylic acid as the gelling agent including the following constituent parts by weight %:

| | |
|---|---|
| co-polymer of tetraallylpentaerythrate acrylic acid | 2.0–4.5 |
| glycerin | 10.0–20.0 |
| surface active agent | 0.9–1.1 |
| sodium monofluorophosphate | 0.7–5.0 |
| anticaries agent | 2.0–6.0 |
| flavour | 0.9–1.0 |
| water | the rest | at pH=6.5–7.5.

* * * * *